United States Patent
Ono et al.

(10) Patent No.: US 6,930,204 B2
(45) Date of Patent: Aug. 16, 2005

(54) PROCESS FOR PRODUCING A CYCLIC ALIPHATIC OXIME

(75) Inventors: Mitsuji Ono, Okayama-ken (JP); Hajime Nagahara, Kurashiki (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 38 days.

(21) Appl. No.: 10/468,890

(22) PCT Filed: Feb. 26, 2002

(86) PCT No.: PCT/JP02/01731

§ 371 (c)(1),
(2), (4) Date: Dec. 12, 2003

(87) PCT Pub. No.: WO02/068378

PCT Pub. Date: Sep. 6, 2002

(65) Prior Publication Data

US 2004/0116746 A1 Jun. 17, 2004

(30) Foreign Application Priority Data

Feb. 26, 2001 (JP) ........................................ 2001-050220
Jun. 20, 2001 (JP) ........................................ 2001-186773

(51) Int. Cl.$^7$ ...................... C07C 249/04; C07C 251/44
(52) U.S. Cl. ........................................ 564/253; 564/262
(58) Field of Search ................................... 564/253, 262

(56) References Cited

U.S. PATENT DOCUMENTS 4,504,681 A    3/1985  Armor
5,684,201 A  * 11/1997 Rieber et al. ................ 564/267

FOREIGN PATENT DOCUMENTS

EP            395046 A2    10/1990

OTHER PUBLICATIONS

Database CAPLUS on STN, Yasui et al., JP 47025324 (Jul. 11, 1972) (abstract).*
Catalogue of the capillary column ( trade name: DB–1701, manufactured and sold by J&W Scientific, U.S.A.) (Jul. 25, 2001).

* cited by examiner

*Primary Examiner*—Brian Davis
(74) *Attorney, Agent, or Firm*—Birch, Stewart, Kolasch & Birch, LLP

(57) ABSTRACT

Disclosed is a method for producing a cyclic aliphatic oxime, which comprises subjecting a cyclic aliphatic primary amine to oxidation in the liquid phase under superatmospheric pressure in the presence of molecular oxygen and a solid catalyst, wherein the solid catalyst comprises an oxide of at least one metal (a) selected from the group consisting of metals belonging to Groups 5 and 6 of the Periodic Table.

12 Claims, No Drawings

PROCESS FOR PRODUCING A CYCLIC ALIPHATIC OXIME

This application is the national phase under 35 U.S.C. § 371 of PCT International Application No. PCT/JP02/01731 which has an International filing date of Feb. 26, 2002, which designated the United States of America.

BACKGROUND OF THE INVENTION

1. Field of the Invention

The present invention relates to a method for producing a cyclic aliphatic oxime. More particularly, the present invention is concerned with a method for producing a cyclic aliphatic oxime, which comprises subjecting a cyclic aliphatic primary amine to oxidation in the liquid phase under superatmospheric pressure in the presence of molecular oxygen and a solid catalyst, wherein the solid catalyst comprises an oxide of at least one metal (a) selected from the group consisting of metals belonging to Groups 5 and 6 of the Periodic Table. The method of the present invention is advantageous not only in that the oxidizing agent employed is molecular oxygen which is much safer than other oxidizing agents (such as hydrogen peroxide and an organic hydroperoxide), but also in that it becomes possible to produce a cyclic aliphatic oxime in the liquid phase with high selectivity. Further, since a solid catalyst is used in the method of the present invention, the separation and recovery of the catalyst from the reaction mixture can be very easily performed after the reaction without any cumbersome operations.

2. Prior Art

A cyclic aliphatic oxime is a compound which is useful as an antioxidant or the like, but it is also widely used as a raw material of products (such as medicines and agricultural chemicals) related to the field of organic industrial chemistry. A cyclic aliphatic oxime is obtained by an oxidation of a cyclic aliphatic primary amine and, for example, when the cyclic aliphatic primary amine is cyclohexylamine, cyclohexanone oxime is obtained as a corresponding cyclic aliphatic oxime. Cyclohexanone oxime is a commercially important compound which is used as not only an antioxidant, but also an intermediate of ε-caprolactam which is a raw material of nylon-6.

As conventional methods for producing an oxime by oxidizing an alicyclic or aliphatic primary amine, there can be mentioned a method in which an alicyclic or aliphatic primary amine is reacted with hydrogen peroxide in the presence of an inorganic salt catalyst comprising molybdenum, tungsten or uranium as an active metal species; and a method in which an alicyclic or aliphatic primary amine is reacted with an organic hydroperoxide in an organic solvent in the presence of a catalyst comprising titanium, molybdenum, tungsten and vanadium. When these conventional methods which employ hydrogen peroxide or an organic hydroperoxide as an oxidizing agent are practiced on a commercial scale, the oxidizing agent is handled by a conventional manner of operation, which is dangerous due to the very high reactivity of such oxidizing agent. In addition, when an organic hydroperoxide is used, since by-products formed by the reduction of the organic hydroperoxide are contained in the resultant reaction mixture, the separation and purification of the desired oxime become cumbersome.

In order to solve the above-mentioned problems, the following methods (1) to (4) which use molecular oxygen (such as air or oxygen gas) as an oxidizing agent have been proposed:

(1) a method in which a water-soluble salt of molybdenum, tungsten and/or uranium is used as a catalyst, and a primary amine is subjected to photo-oxidization in the presence of water and molecular oxygen by using a mercury lamp (see German Patent No. 1021358);

(2) a method in which a primary amine is subjected to oxidation under superatmospheric pressure in the presence of a catalyst, a tertiary alcohol and molecular oxygen, and preferably, further in the presence of gaseous ammonia, wherein the catalyst is tungstic acid, phosphotungstic acid, molybdic acid, selenic acid, selenious acid and the like (see Examined Japanese Patent Application Publication No. Sho 47-25324);

(3) a method in which a primary amine is subjected to oxidation in the gaseous phase in the presence of a catalyst and molecular oxygen, wherein the catalyst is a silica gel, alumina catalyst or a solid catalyst comprising alumina and tungsten oxide (see U.S. Pat. Nos. 4,337,358, 4,504,681, 4,560,797 and 4,624,939); and (4) a method in which a primary amine is subjected to oxidation in the liquid phase under superatmospheric pressure in the presence of a homogeneous or heterogeneous catalyst comprising a metal belonging to Group 4 of the Periodic Table, and molecular oxygen (see European Patent No. 395046).

However, these methods (1) to (4) have the following defects. The above-mentioned method (1) requires the use of light and, thus, this method requires not only a large amount of electricity, but also a cumbersome operation for the maintenance of a light source, such as a mercury lamp. Further, in methods (1) and (2), a homogeneous catalyst is generally employed and, thus, these methods have a problem in that the separation of the catalyst from the reaction system after the reaction becomes difficult.

The reaction in method (3) is a heterogeneous reaction which uses a solid catalyst. Since the heterogeneous reaction is performed in the gaseous phase under relatively stringent conditions, namely at a reaction temperature of 120 to 250° C., it is considered that the catalyst is easily deactivated. The present inventors have studied this method and found that, when the reaction is performed in the gaseous phase at a reaction temperature of 160° C. or more, the catalyst is easily deactivated by the accumulation of the by-products on the surface of the catalyst, wherein the by-products include tar-like by-products (which are considered to be derived from the produced oxime) and other high boiling point organic compounds.

Further, it is known that an oxidation reaction of a cyclic aliphatic primary amine is an exothermic reaction, and an oxime which is a desired product is thermally unstable. Therefore, for performing an oxidation of a cyclic aliphatic primary amine on a commercial scale, a reaction in the liquid phase is advantageous over a reaction in the gaseous phase, because the heat of reaction can be removed more easily from the liquid phase. Further, there is a demand for the development of a method in which the reaction can be performed not only under mild temperature conditions (i.e., at low temperatures) which suppress the gradual decomposition of the produced oxime, but also by using a heterogeneous catalyst which can be easily separated from the reaction mixture.

With respect to the above-mentioned method (4), the above-mentioned European Patent No. 395046 discloses a method in which a primary amine is oxidized in the liquid phase under superatmospheric pressure in the presence of a heterogeneous catalyst comprising a metal belonging to Group 4 of the Periodic Table. In this patent document, reactions using titanium oxide and the like as the heterogeneous catalyst are exemplified. However, the selectivity for the produced oxime is as low as approximately 30 to 50%.

As apparent from the above, the conventional methods had the following problems. With respect to the methods for producing an oxime by using a peroxide as an oxidizing agent, the use of the peroxide is dangerous and cumbersome operations are necessary. Further, the above-mentioned methods (1) to (4) which use molecular oxygen as an oxidizing agent had problems, such that a cumbersome operation is needed for the separation of the catalyst, that the catalyst is easily deactivated, and that the selectivity for oxime is low. Therefore, it has been desired to develop a method which has advantages that the deactivation of the catalyst can be suppressed, that an oxime can be produced with high selectivity even when the reaction is performed at relatively low temperatures, and that a solid catalyst, which can be easily separated from the reaction mixture, is used.

SUMMARY OF THE INVENTION

The present inventors have made extensive and intensive studies for solving the above-mentioned problems. As a result, it has been found that a cyclic aliphatic oxime can be produced with high selectivity when a cyclic aliphatic primary amine is subjected to oxidation in the liquid phase under superatmospheric pressure in the presence of molecular oxygen and a solid catalyst, wherein the solid catalyst comprises an oxide of at least one metal (a) selected from the group consisting of metals belonging to Groups 5 and 6 of the Periodic Table. Specifically, when the above-mentioned solid catalyst is used in the production of a cyclic aliphatic oxime, which is conducted in the liquid phase, it becomes possible to produce a cyclic aliphatic oxime with high selectivity which is generally not less than 50%, preferably not less than 70%. Further, since a solid catalyst is used, the separation of the catalyst from the reaction mixture can be very easily performed after the reaction without any cumbersome operations.

The present invention has been completed, based on these novel findings.

Accordingly, it is an object of the present invention to provide a method which is advantageous not only in that the oxidizing agent employed is molecular oxygen which is much safer than other oxidizing agents (such as hydrogen peroxide and an organic hydroperoxide), but also in that it becomes possible to produce a cyclic aliphatic oxime in the liquid phase with high selectivity.

The forgoing and other objects, features and advantages of the present invention will be apparent to those skilled in the art from the following detailed description and the appended claims.

DETAILED DESCRIPTION OF THE INVENTION

In the present invention, there is provided a method for producing a cyclic aliphatic oxime, which comprises subjecting a cyclic aliphatic primary amine to oxidation in the liquid phase under superatmospheric pressure in the presence of molecular oxygen and a solid catalyst, wherein the solid catalyst comprises an oxide of at least one metal (a) selected from the group consisting of metals belonging to Groups 5 and 6 of the Periodic Table.

For easy understanding of the present invention, the essential features and various preferred embodiments of the present invention are enumerated below.

1. A method for producing a cyclic aliphatic oxime, which comprises subjecting a cyclic aliphatic primary amine to oxidation in the liquid phase under superatmospheric pressure in the presence of molecular oxygen and a solid catalyst, wherein the solid catalyst comprises an oxide of at least one metal (a) selected from the group consisting of metals belonging to Groups 5 and 6 of the Periodic Table.
2. The method according to item 1 above, wherein the cyclic aliphatic primary amine is cyclohexylamine.
3. The method according to item 1 or 2 above, wherein the solid catalyst further comprises an oxide of at least one metal (b) selected from the group consisting of metals belonging to Groups 2, 13 and 14 of the Periodic Table.
4. The method according to item 3 above, wherein the metal (a) is at least one metal selected from the group consisting of niobium and tungsten.
5. The method according to item 3 above, wherein the metal (a) is tungsten.
6. The method according to any one of items 3 to 5 above, wherein the metal (b) is at least one metal selected from the group consisting of aluminum and silicon.
7. The method according to any one of items 1 to 6 above, wherein the content of the metal (a) in the solid catalyst is from 1 to 60% by weight.
8. The method according to item 1 or 2 above, wherein the solid catalyst further comprises an oxide of at least one metal (c) selected from the group consisting of metals belonging to Group 4 of the Periodic Table.
9. The method according to item 8 above, wherein the metal (a) is at least one metal selected from the group consisting of niobium, tantalum and tungsten.
10. The method according to item 8 above, wherein the metal (a) is tungsten.
11. The method according to any one of item 8 to 10 above, wherein the metal (c) is at least one metal selected from the group consisting of titanium and zirconium.
12. The method according to any one of item 8 to 11 above, wherein the atomic ratio of the metal (a) to the metal (c) is in the range of from 0.01 to 1.0.

Hereinbelow, the present invention will be described in more detail.

The method of the present invention is a method for producing a cyclic aliphatic oxime by subjecting a cyclic aliphatic primary amine to oxidization. With respect to the cyclic aliphatic primary amine used in the present invention, there is no particular limitation; however, it is preferred to use saturated cyclic aliphatic primary amines. Specific examples of saturated cyclic aliphatic primary amines include cyclohexylamine, cyclooctylamine, cyclopentylamine, cycloheptylamine and cyclododecanylamine. With respect to cyclic aliphatic oximes which can be produced from the above-mentioned saturated cyclic aliphatic primary amines, cyclohexanone oxime can be produced from cyclohexylamine; cyclooctanone oxime can be produced from cyclooctylamine; cyclopentanone oxime can be produced from cyclopentylamine; cyclododecanone oxime can be produced from cycloheptylamine; and methylhexanone oxime can be produced from cyclododecanylamine. Further examples of cyclic aliphatic primary amines include cyclic aliphatic primary amines (such as methylcyclohexylamine) which have an aliphatic ring substituted with a group (such as an alkyl group) which is inert under the reaction conditions.

In the present invention, cyclohexylamine is most preferred as the cyclic aliphatic primary amine. With respect to the method for producing a cyclohexylamine, there is no particular limitation. Examples of methods for producing cyclohexylamine include a method in which a direct amination of cyclohexene by $NH_3$ is performed to produce cyclohexylamine {see Unexamined Japanese Patent Application Laid-Open Specification No. Sho 57-4948 (corresponding to EP 39918), Unexamined Japanese Patent Application Laid-Open Specification No. Sho 64-75453 (corresponding to EP 3(35564), Unexamined Japanese Patent Application Laid-Open Specification No. Hei 9-194438 (corresponding to EP 785185), Unexamined Japanese Patent Application Laid-Open Specification No. Hei 10-72409 (corresponding to EP 802176) and Unexamined Japanese Patent Application Laid-Open Specification No. Hei 10-291968 (corresponding to EP 846675)]; a method in which an amination of cyclohexanol by $NH_3$ is performed to produce cyclohexylamine {see Examined Japanese Patent Application Publication Nos. Sho 41-7575, Sho 51-41627, Sho 51-32601 (corresponding to U.S. Pat. No. 3,520,933) and Unexamined Japanese Patent Application Laid-Open Specification No. Hei 6-1758}; and a method in which a hydrogenation of aniline, nitrobenzene, nitrocyclohexane or the like is performed to produce cyclohexylamine.

With respect to the purity of cyclohexylamine, there is no particular limitation, and no particular problem is caused by the presence of a small amount of impurities, such as water and organic compounds (e.g., cyclohexanol, dicyclohexylamine, nitrocyclohexane and N-cyclohexylidene-cyclohexylamine) which are by-produced in the above-mentioned method for producing cyclohexylamine. However, it is preferred that the total concentration of the by-produced organic compounds contained in cyclohexylamine is not more than 5 mol %. The water content of cyclohexylamine is preferably in the range such that the liquid phase does not become heterogeneous under the reaction conditions employed. In other words, in the method of the present invention, when the oxidation reaction is performed using a solvent mentioned below, it is preferred that, under the reaction conditions employed, the liquid phase does not separate into an aqueous phase comprising water as a major component and an organic solvent phase comprising an organic solvent as a major component.

The solid catalyst used in the method of the present invention is a solid catalyst comprising an oxide of at least one metal (a) selected from the group consisting of metals belonging to Groups 5 and 6 of the Periodic Table. The metals belonging to Groups 5 and 6 of the Periodic Table not only have been used as catalysts for a denitration-desulfurization reaction, but also have been widely used as catalysts for oxidation reactions of organic compounds. In conventional catalytic oxidation reactions performed in the gaseous phase in the presence of a catalyst comprising an oxide of the above-mentioned metal (a), and molecular oxygen (such as oxygen gas or air) as an oxidizing agent, it is necessary to perform the reaction at high temperatures which are 200° C. or higher. The reason for this is considered to reside in that a large amount of activation energy is needed to convert the molecular oxygen into an active oxygen species by the action of the metal oxide catalyst. As a conventional method for performing an oxidation reaction of aliphatic or alicyclic amines in the presence of an oxidation catalyst, there has been known a method in which a liquid phase reaction is performed in the presence of a compound comprising a metal belonging to Group 5 of the Periodic Table and/or a metal belonging to Group 6 of the Periodic Table. However, as mentioned above, in such a conventional method, a strong oxidizing agent, such as an organic hydroperoxide, must be used as an oxidizing agent.

As in the case of method (3) described above under the section "Prior Art", there is known a method in which a heterogeneous reaction is performed by subjecting an aliphatic or alicyclic amine to oxidization in the gaseous phase in the presence of molecular oxygen and a solid catalyst comprising tungsten oxide. On the other hand, it has been attempted to perform an oxidation reaction in the liquid phase in the presence of a solid catalyst comprising a combination of tungsten oxide and alumina {JOURNAL OF CATALYSIS 83, 487–490 (1983)}. In such a method, a cyclohexylamine solution and a solid catalyst were heated under reflux conditions and under a low pressure which is below atmospheric pressure, while introducing oxygen into the reaction system; however, an oxidation reaction does not proceed. From this result, it has been considered that a solid catalyst comprising an oxide of a metal belonging to Group 5 of the Periodic Table and/or a metal belonging to Group 6 of the Periodic Table cannot be used as an effective catalyst for the oxidation of a cyclic aliphatic amine in the liquid phase in the presence of molecular oxygen.

However, the present inventors have made extensive and intensive studies on the catalyst and reaction conditions for the oxidation reaction of a cyclic aliphatic primary amine in the liquid phase. As a result, it has surprisingly been found that when a cyclic aliphatic primary amine is subjected to oxidation in the liquid phase under superatmospheric pressure, namely conditions wherein molecular oxygen is present in the liquid phase, in the presence of a solid catalyst comprising an oxide of at least one metal (a) selected from the group consisting of metals belonging to Groups 5 and 6 of the Periodic Table, a cyclic aliphatic oxime can be produced with high selectivity.

With respect to at least one metal (a) of the solid catalyst used in the present invention, which is selected from the group consisting of metals belonging to Groups 5 and 6 of the Periodic Table, examples thereof include chromium (Cr), niobium (Nb), tantalum (Ta), molybdenum (Mo) and tungsten (W).

It is preferred that the solid catalyst used in the present invention further comprises an oxide of another metal which is different from metal (a). Specifically, as two preferred species of the solid catalysts used in the present invention, there can be mentioned:

(α) a solid catalyst comprising an oxide of at least one metal (a) selected from the group consisting of metals belonging to Groups 5 and 6 of the Periodic Table, and an oxide of at least one metal (b) selected from the group consisting of metals belonging to Groups 2, 13 and 14 of the Periodic Table; and (β) a solid catalyst comprising an oxide of at least one metal (a) selected from the group consisting of metals belonging to Groups 5 and 6 of the Periodic Table, and an oxide of at least one metal (c) selected from the group consisting of metals belonging to Group 4 of the Periodic Table.

Firstly, an explanation is made on the above-mentioned solid catalyst (α).

With respect to the solid catalyst (α) which is one of the preferred species of the solid catalysts used in the present invention, metal (a) is preferably Nb and/or W, more preferably W.

With respect to metal (b) used in the solid catalyst (α), there is no particular limitation so long as metal (b) is at least one metal selected from the group consisting of metals belonging to Groups 2, 13 and 14 of the Periodic Table. Examples of metal (b) include magnesium (Mg), calcium (Ca), barium (Ba), boron (B), aluminum (Al), gallium (Ga)

and silicon (Si). Of these, Al and Si are especially preferred. As oxides of metal (b), there can be mentioned single metal oxides, such as MgO, CaO, BaO, $Al_2O_3$ and $SiO_2$, and compound oxides, such as $SiO_2$—$Al_2O_3$, $B_2O_3$—$Al_2O_3$, $Ga_2O_3$—$SiO_2$, MgO—$SiO_2$ and CaO—$SiO_2$. As further examples of metal (b), there can be mentioned aluminosilicates, and synthetic and natural zeolites having various porous structures. $Al_2O_3$ and $SiO_2$ are preferred as the single metal oxide, and $SiO_2$—$Al_2O_3$ is preferred as the compound oxide.

Solid catalyst (α) can be a simple mixture obtained by physically mixing an oxide of metal (a) with an oxide of metal (b) by kneading method, but it is preferred that the solid catalyst (α) is either a carrier-supported catalyst in which an oxide of metal (a) is supported on an oxide of metal (b) or a catalyst obtained by the sol-gel method described in U.S. Pat. No. 4,624,939.

The following method is an example of a method for preparing a carrier-supported catalyst in which an oxide of metal (a) is supported on an oxide of metal (b). In the preparation of the carrier-supported catalyst, a precursor of an oxide of metal (a) is used. Examples of precursors include a halide, an oxyhalide, an alkoxide, a nitrate, a hydroxide, a carboxylate, a sulfate, an oxide and a carbonate of at least one metal (a) (Cr, Nb, Ta, Mo, W and the like). When an oxide of Nb and/or an oxide of Ta is used as an oxide of metal (a), an acidic complex of metal (a) or an ammonium salt thereof (see Unexamined Japanese Patent Application Laid-Open Specification No. Hei 7-309787) can be also used as a precursor (wherein the acidic complex of metal (a) is, for example, an acidic complex of Nb and oxalic acid or tartaric acid, which complex is obtained by subjecting a niobium halide to hydrolysis to thereby obtain a hydrate of an oxidized niobium gel, and dissolving the obtained oxidized niobium gel in an aqueous solution of oxalic acid or tartaric acid). Further, when an oxide of Nb is used as an oxide of metal (a), acidic compounds, such as niobium hydrogen oxalate $\{(NbHC_2O_4)_5\}$, can be also used as a precursor. When an oxide of W is used as an oxide of metal (a), oxyammonium salts, such as ammonium paratungstate and ammonium metatungstate, and an alkali metal salt of tungstic acid can be used as a precursor. The precursor of metal (a) is dissolved in an appropriate solvent, such as water or alcohol, to thereby obtain a solution. Then, an oxide carrier comprising the above-mentioned oxide of metal (b) ($Al_2O_3$, $SiO_2$, $SiO_2$—$Al_2O_3$ or the like) is immersed in the obtained solution of the precursor of metal (a), and the oxide of metal (a) is caused to be supported on the carrier comprising an oxide of metal (b) by a conventional impregnation method (e.g., solidification by evaporation-drying) or an adsorption method (e.g., equilibrium adsorption), thereby obtaining a catalyst precursor. The obtained catalyst precursor is dried at a temperature in the range of from room temperature to approximately 150° C. (if necessary, under reduced pressure) to remove the solvent. Subsequently, the dried catalyst precursor is calcined in the gaseous phase under a flow of pure oxygen, air or other oxygen-containing gas at approximately 300 to 500° C., thereby obtaining solid catalyst (α) in which the oxide of metal (a) is supported on the oxide of metal (b). When it is intended to support oxides of two or more types of metal (a) on an oxide of metal (b), the oxides of two or more types of metal (a) can be caused to be supported on the carrier either simultaneously or in a stepwise manner.

As preferred examples of oxide carriers used in the above-mentioned method, there can be mentioned $Al_2O_3$, $SiO_2$ and $SiO_2$—$Al_2O_3$. It is preferred that the oxide carrier has a large specific surface area, specifically a specific surface area of 100 $m^2/g$ or more, more advantageously 200 $m^2/g$ or more. When $Al_2O_3$ is used alone as a carrier, γ-$Al_2O_3$ is preferred.

As a specific example of method for preparing a solid catalyst comprising an oxide of metal (a) and an oxide of metal (b) by the sol-gel method, there can be mentioned the following method. An aqueous solution containing a soluble salt of at least one metal (a) (Cr, Nb, Ta, Mo, W and the like) is mixed with an alkoxide of at least one metal (b) (Al, Si and the like) to thereby effect a hydrolysis reaction. The resultant mixture is dried at a temperature in the range of from room temperature to 150° C. (if necessary, under reduced pressure) to remove water and a by-produced alcohol to obtain a gel-like product. The obtained gel-like product is calcined in the gaseous phase under a flow of pure oxygen, air or another oxygen-containing gas at a high temperature, to thereby obtain a solid catalyst. The structure of the solid catalyst obtained by the sol-gel method mentioned above has not yet been elucidated, but it is considered that the solid catalyst comprises a compound of metal (a) oxide with metal (b) oxide (that is, a structure in which metal (a) atoms and metal (b) atoms are chemically bonded to one another through oxygen atoms).

With respect to the sol-gel method, reference can be made to U.S. Pat. No. 4,624,939 which discloses a method for producing a catalyst by using an oxygen-containing tungsten compound and alumina, and a solid catalyst obtained by this method can be also used in the present invention. In the above-mentioned U.S. Pat. No. 4,624,939, the obtained catalyst is used for producing an oxime by subjecting a cyclic aliphatic amine to oxidation at high temperatures in the gaseous phase in the presence of molecular oxygen. However, it has not been considered that the solid catalyst obtained in the above-mentioned patent document is effective for an oxidation reaction (such as performed in the method of the present invention) which is performed at relatively low temperatures in the liquid phase. From the studies of the present inventors, it has, for the first time, become apparent that the catalyst disclosed in the above-mentioned U.S. patent can be advantageously used for the above-mentioned oxidation reaction performed in the method of the present invention.

In the case of a solid catalyst comprising both of a metal (a) oxide and a metal (b) oxide, it is preferred that the metal (a) content of the solid catalyst is 1 to 60% by weight, more preferably 2 to 40% by weight. When the metal (a) content is less than the above-mentioned range, the selectivity for a cyclic aliphatic oxime is likely to be lowered, and when the metal (a) content exceeds the above-mentioned range, the reaction rate is likely to be markedly lowered. In the present invention, the content of metal (a) of the solid catalyst can be measured by the absolute calibration method using a fluorescent X-ray analyzer.

In the case of a solid catalyst wherein a metal (a) oxide is supported on a metal (b) oxide, it is more preferred that the metal (a) content of the solid catalyst is 2 to 30% by weight. In the case of a solid catalyst produced by the above-mentioned sol-gel method, it is more preferred that the metal (a) content of the solid catalyst is 3 to 40% by weight.

Further, with respect to the solid catalyst used in the present invention, the atomic ratio of metal (a) to metal (b) (namely, the atomic ratio of a metal belonging to Group 5 of the Periodic Table and/or a metal belonging to Group 6 of the Periodic Table, relative to a metal belonging to Group 2 of the Periodic Table, a metal belonging to Group 13 of the Periodic Table and/or a metal belonging to Group 14 of the Periodic Table) is preferably in the range of from 0.002 to 3.0, more preferably from 0.005 to 1.0.

Next, an explanation is made on the above-mentioned solid catalyst (β).

With respect to solid catalyst (β) which is another preferred species of the solid catalyst used in the present invention, metal (a) is preferably Nb, Ta and/or W, more preferably W.

As examples of metal (c) used in solid catalyst (β), there can be mentioned titanium (Ti), zirconium (Zr) and hafnium (Hf). As oxides of. metal (c) contained in solid catalyst (β), single metal oxides, such as $TiO_2$ and $ZrO_2$, and compound oxides, such as $TiO_2$—$ZrO_2$, are preferred. With respect to $TiO_2$ and $ZrO_2$, these oxides may contain $SiO_2$ as an impurity.

Solid catalyst (β) can be a mixture obtained by physically combining an oxide of metal (a) and an oxide of metal (c) by kneading method, but it is preferred that solid catalyst (β) is either a carrier-supported catalyst in which an oxide of metal (a) is supported on an oxide of metal (c) or a compound oxide comprising both metals (a) and (c)

The following method is an example of a method for preparing a carrier-supported catalyst wherein an oxide of metal (a) is supported on an oxide of metal (c). In the preparation of the carrier-supported catalyst, a precursor of an oxide of metal (a) is used. Examples of precursors include a halide, an oxyhalide, an alkoxide and a hydroxide of metal (a) (Nb, Ta, W and the like). When an oxide of W is used as an oxide of metal (a), oxyammonium salts, such as ammonium paratungstate and ammonium metatungstate, and an alkali metal salt of tungstic acid can be used as a precursor. When an oxide of Nb and/or an oxide of Ta is used as an oxide of metal (a), an acidic complex of metal (a) or an ammonium salt thereof (see Unexamined Japanese Patent Application Laid-Open Specification No. Hei 7-309787) can be also used as a precursor (wherein the acidic complex of metal (a) is, for example, an acidic complex of Nb and oxalic acid or tartaric acid, which complex is obtained by subjecting a niobium halide to hydrolysis to thereby obtain a hydrate of an oxidized niobium gel, and dissolving the obtained oxidized niobium gel in an aqueous solution of oxalic acid or tartaric acid). When an oxide of Nb is used as an oxide of metal (a), acidic compounds, such as hydrogen niobium oxalate $\{(NbHC_2O_4)_5\}$, can be also used as a precursor. The precursor of metal (a) is dissolved in an appropriate solvent, such as water or alcohol, to thereby obtain a solution. Then, a source of an oxide of at least one metal (c) (Ti, Zr and the like) is immersed in the obtained solution containing metal (a) to obtain a mixture of metal (a) precursor and metal (c) oxide. The source of metal (c) oxide can be a solid oxide, an oxide sol or a hydroxide of at least one metal (c), and these compounds can be used individually or in combination, i.e., as a mixture containing predetermined amounts of several compounds. Alternatively, a solid $TiO_2$—$ZrO_2$ compound oxide which has been prepared in advance can also be used. Using the above-mentioned mixture of metal (a) precursor and metal (c) oxide, metal (a) is caused to be supported on the metal (c) oxide by a conventional impregnation method (e.g., solidification by evaporation drying) or an adsorption method (e.g., equilibrium adsorption), thereby obtaining a catalyst precursor. The obtained catalyst precursor is dried at a temperature in the range of from room temperature to approximately 150° C. (and if necessary, under reduced pressure) to remove the solvent. Subsequently, the dried catalyst precursor is calcined in the gaseous phase under a flow of pure oxygen, air or another oxygen-containing gas at approximately 300 to 500° C., to thereby obtain solid catalyst (β) comprising metal (c) oxide having supported thereon metal (a) oxide. When it is intended to support oxides of two or more types of metal (a) on the metal (c) oxide, the oxides of two or more types of metal (a) can be caused to be supported on the carrier either simultaneously or in a stepwise manner.

When $TiO_2$ is used as an oxide of metal (c) in the above-mentioned method for obtaining a carrier-supported catalyst, it is preferred that the source of $TiO_2$ is a compound having a large specific surface area, such as a $TiO_2$ having an anatase crystal structure or amorphous $TiO_2$, or titanium hydroxide. For preparing a solid catalyst comprising $ZrO_2$ as an oxide of metal (c), it is preferred that the source of $ZrO_2$ is a compound having a large specific surface area, such as a $ZrO_2$ of a monoclinic system or a tetragonal system, or a zirconium hydroxide represented by a general formula:

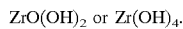

$$ZrO(OH)_2 \text{ or } Zr(OH)_4.$$

As described above, in the method of the present invention, a compound oxide comprising metals (a) and (c) can be used as a solid catalyst. In the present invention, the "compound oxide comprising metals (a) and (c)" means an oxide comprising metal (a), metal (c) and oxygen, and has a structure in which metal (a) atoms and metal (c) atoms are chemically bonded to one another through oxygen atoms. Such structure of the compound oxide can be confirmed by an elemental analysis.

As specific examples of the above-mentioned structure, there can be mentioned a structure in which a metal (a) atom in the form of an oxo-acid ion is chemically bonded to a metal (c) atom, and a structure in which a part of metal (c) atoms in the metal (c) oxide is replaced by a metal (a) atom. For example, a catalyst comprising an oxide of tungsten and zirconium is described in JOURNAL OF CATALYSIS 168, 431–441 (1997) and JOURNAL OF THE CHEMICAL SOCIETY FARADAY TRANSACTIONS 90 (1), 193–202 (1994).

The compound oxide which can be used as solid catalyst (β) in the present invention is considered to exhibit acidic properties (i.e., the strength and amount of acid sites formed on the surface of a solid) which are different from those of a simple mixture obtained by physically mixing a metal (a) oxide with a metal (c) oxide which has been formed separately from the metal (a) oxide. For example, a compound oxide comprising tungsten as metal (a) and titanium or zirconium as metal (c) is known to exhibit specific acidic properties due to chemical interaction. By utilizing such specific acidic properties, the above-mentioned compound oxide has conventionally been used as a solid catalyst for performing various heterogeneous reactions, such as dehydration of alcohols, hydration of olefins and skeletal isomerization of alkanes.

The present inventors have made extensive and intensive studies on the catalyst and reaction conditions for the oxidation reaction of a cyclic aliphatic primary amine in the liquid phase. As a result, it has surprisingly been found that the above-mentioned compound oxide, namely a compound oxide comprising at least one metal (a) selected from the group consisting of metals belonging to Groups 5 and 6 of the Periodic Table and at least one metal (c) selected from the group consisting of metals belonging to Group 4 of the Periodic Table, also can be used effectively as a solid catalyst for performing the above-mentioned oxidation reaction.

When solid catalyst (β) is a compound oxide, there is no particular limitation with respect to the oxidation state of metal (a) which is present in the form of an oxide thereof, and metal (a) may have any of positive oxidation numbers of the chemical species of metal (a).

With respect to a method for producing a compound oxide used as solid catalyst (β), there is no particular limitation, and any conventional methods for producing a catalyst can be employed. Specifically, solid catalyst (β) can be produced by the coprecipitation method or the sol-gel method, which are explained below.

1) Coprecipitaion Method

First, a precursor of an oxide of at least one metal (a) and a precursor of an oxide of at least one metal (c) are dissolved in an aqueous medium to thereby obtain an aqueous solution containing the precursors in a predetermined ratio. As a precursor of the metal (a) oxide, it is preferred to use a soluble salt of metal (a) (Nb, Ta, W and the like) or a compound which is soluble in an aqueous medium. Examples of precursors include an ammonium salt, a halide, an oxyhalide, a nitrate, a carboxylate, a sulfate, an oxide and a carbonate of at least one metal (a). As a precursor of the metal (c) oxide ($TiO_2$, $ZrO_2$, $TiO_2$—$ZrO_2$ or the like), it is preferred to use a soluble metal compound which is soluble in an aqueous medium. For example, for preparing a catalyst comprising $TiO_2$ as the metal (c) oxide, titanium tetrachloride, titanium sulfate, titanium oxalate or the like can be used as a precursor of $TiO_2$. For preparing a catalyst comprising $ZrO_2$ as the metal (c) oxide, zirconium tetrachloride, zirconium oxychloride or the like can be used as a precursor of $ZrO_2$.

Next, the above-obtained aqueous solution is stirred, while maintaining the temperature of the solution at 60° C. or less, followed by addition of an aqueous solution of a basic compound in an amount such that the final pH value of the resultant solution becomes 5 to 11, thereby obtaining a slurry containing a precipitate composed of a precursor of the metal (a) oxide and a precursor of the metal (c) oxide (hereinafter, this slurry is referred to as a "coprecipitate slurry"). Examples of basic compounds used to neutralize the aqueous solution and cause precipitation include ammonia, sodium hydroxide, potassium hydroxide, sodium carbonate and potassium carbonate. From the viewpoint of ease in handling the coprecipitate slurry, it is preferred to use an aqueous solution of ammonia (aqueous ammonia). When the aqueous solution of metal (a) is a basic solution, the precipitate can be formed by simultaneously adding an aqueous solution containing metal (a) and aqueous ammonia to the aqueous solution of the precursor of the metal (c) oxide.

The precipitate obtained by the above operation, which is composed of the precursor of the metal (a) oxide and the precursor of the metal (c) oxide, is separated from the coprecipitate slurry. The separated precipitate is washed thoroughly and dried at a temperature in the range of from room temperature to approximately 150° C. (and if necessary, under reduced pressure). Subsequently, the dried precipitate is calcined in the gaseous phase under a flow of pure oxygen, air or another oxygen-containing gas at approximately 300 to 700° C., to thereby obtain a compound oxide comprising metals (a) and (c).

2) Sol-Gel Method

An alkoxide of at least one metal (a) and an alkoxide of at least one metal (c) are mixed together in a predetermined ratio, and the resultant mixture is dissolved in a non-aqueous solvent (such as a lower alcohol), optionally while heating, to thereby obtain a uniform solution. The ligand (alkoxy group) of the metal (a) alkoxide and that of the metal (c) alkoxide may be the same or different. Examples of ligands of the metal alkoxides include a methoxy group, an ethoxy group, an n-propoxy group, an isopropoxy group and a sec-butoxy group. The solubilities of different metal alkoxides vary depending on the type of the ligand and the type of the solvent. Therefore, an appropriate combination of the ligand and the solvent can be selected in accordance with the type of the metal species used, such that a uniform solution can be obtained.

To the above-obtained uniform solution is added deionized water for hydrolysis and, if desired, an aqueous solution of a monoalcohol. The resultant mixture is agitated to effect the hydrolysis of the metal alkoxides, thereby obtaining a gel. In general, the hydrolysis is completed within several hours at room temperature, but the reaction system can be heated to shorten the time necessary for the hydrolysis. In addition, for improving the rate of hydrolysis, an acid or base (such as nitric acid or aqueous ammonia) can be added in an amount which is sufficient for the acid or base to function as a catalyst (in general, of the acid or base is used in an amount of 0.1 to 0.01, in terms of a molar ratio of the acid or base to the total of the metal alkoxides).

Next, the obtained gel is withdrawn from the reaction system and dried at a temperature in the range of from room temperature to approximately 150° C. (and if necessary, under reduced pressure) to remove any by-produced alcohol derived from the hydrolyzed ligands, the solvent and excess water. The dried gel is subjected to calcination at approximately 300 to 700° C., thereby obtaining a compound oxide comprising metals (a) and (c).

Further, the production of the compound oxide comprising metals (a) and (c) can be conducted by a method in which a solid gel is directly obtained by subjecting a mixture of the alkoxides of metals (a) and (c) to hydrolysis without using any solvent or by using only a very small amount of the above-mentioned non-aqueous solvent. Specifically, for example, a uniform mixture or solution is prepared by mixing an alkoxide of metal (a) and an alkoxide of metal (c) in a predetermined ratio in a dried gaseous phase without using any solvent or by using only a very small amount of the above-mentioned non-aqueous solvent. Next, desalted water is added to the prepared uniform mixture or solution of the metal alkoxides in an amount of at least two equivalents per equivalent of the total of the metal alkoxides used. During the addition of the desalted water, the uniform mixture or solution is vigorously agitated while cooling. The hydrolysis of the alkoxides occurs almost instantaneously, and a cake-like solid gel is formed. Subsequently, the obtained gel is dried at a temperature in the range of from room temperature to approximately 150° C. (and if necessary, under reduced pressure) to remove water and a by-produced alcohol. The dried gel is subjected to calcination at approximately 300 to 700° C., thereby obtaining a compound oxide comprising metals (a) and (c).

In addition, the preparation of the compound oxide comprising metals (a) and (c) can also be conducted by the coordination chemical sol-gel method which is known as one type of the above-mentioned sol-gel methods. The characteristic feature of this method resides in that a crosslinked complex in which atoms of different metals are bonded to one another through diol molecules is formed in a uniform solution. In the complex obtained by this method, different metals are positioned close to each other. Therefore, this method is conventionally used as a technique for obtaining a compound oxide having improved uniformity and a low crystallinity.

Specifically, a uniform solution is prepared by mixing an alkoxide of metal (a) (Nb, Ta, W and the like) and an alkoxide of metal (c) (Ti, Zr and the like) in a predetermined ratio, followed by addition of a diol (crosslinking ligand) as a complexing agent. It is preferred that the diol used as a crosslinking ligand has 2 or more methylene groups positioned between the 2 hydroxyl groups and does not form an insoluble complex by binding a metal atom (Nb, Ta, W or the like) belonging to Group 5 or 6 of the Periodic Table with a metal atom (Ti, Zr or the like) belonging to Group 4 of the Periodic Table. Specifically, it is preferred to use pinacol and/or hexylene glycol as the diol.

In order to replace the ligand (alkoxy group) of each of the metal (a) alkoxide and the metal (c) alkoxide by a diol, a uniform solution obtained by adding desired types of metal alkoxides to a diol is agitated, while heating the solution to approximately 60 to 150° C. For increasing the rate of formation of the complex, any of the following methods can be employed: a method in which a monoalcohol derived from a liberated ligand is removed by continuous distillation, and a method in which a small amount of an ester, such as dimethyl sulfate, is added to the solution as a catalyst.

To the resultant complex-formation reaction mixture is added deionized water for hydrolysis and, if desired, an aqueous solution of a monoalcohol or a diol used as a solvent, thereby hydrolyzing the complex of different metal alkoxides to obtain a gel-like product. Next, the obtained product is fully aged at approximately 100° C. or less. The aged product is dried at a temperature in the range of from approximately 100 to 150° C. under reduced pressure, followed by calcination at approximately 500 to 700° C., thereby obtaining a compound oxide comprising metals (a) and (c).

A compound oxide which can be used as solid catalyst (β) can be prepared by methods other than mentioned above. Specifically, for example, the compound oxide can be prepared by the following method. Using an aqueous solution comprising a soluble salt of metal (a), an alkoxide of metal (c) is instantaneously hydrolyzed while stirring. The resultant product is dried at a temperature in the range of from room temperature to approximately 150° C. (and if necessary, under reduced pressure) to remove water and a by-produced alcohol, thereby obtaining a compound in a gel form. The obtained compound is subjected to calcination in the gaseous phase under a flow of pure oxygen, air or another oxygen-containing gas at approximately 400° C. or more, thereby obtaining a compound oxide of metals (a) and (c).

With respect to solid catalyst (β), it is preferred that the atomic ratio of metal (a) to metal (c) (namely, the atomic ratio of a metal belonging to Group 5 of the Periodic Table and/or a metal belonging to Group 6 of the Periodic Table, relative to a metal belonging to Group 4 of the Periodic Table) is preferably in the range of from 0.01 to 1.0. With respect to solid catalyst (β) used in the present invention, the atomic ratio of metal (a) to metal (c) can be appropriately selected depending on the combination of the metal oxides, and method and conditions used for preparing the catalyst. However, the atomic ratio of metal (a) to metal (c) is more preferably in the range of from 0.015 to 0.5, most preferably from 0.02 to 0.3. The atomic ratio of metal (a) to metal (c) can be determined by measuring each of the amounts of metal (a) and metal (c) present in the catalyst by means of a fluorescent X-ray analyzer.

In the method of the present invention for producing a cyclic aliphatic oxime, a cyclic aliphatic primary amine is subjected to oxidation in the liquid phase under superatmospheric pressure in the presence of molecular oxygen and the solid catalyst.

In the method of the present invention, the oxidation is effected in the liquid phase. The oxidation may be performed without using a solvent so long as the cyclic aliphatic primary amine can be maintained in the liquid state; however, it is preferred that the oxidation is performed in the presence of a solvent. The use of a solvent in the oxidation is advantageous for lowering the amine concentration of the liquid phase to thereby prevent marked occurrence of discoloration of the solid catalyst surface and lowering of the catalyst activity, which are caused by too high a concentration of the amine concentration. Examples of solvents used in the method of the present invention include $C_1$–$C_{10}$ primary, secondary and tertiary alcohols, such as methanol, ethanol, isopropyl alcohol and t-butyl alcohol; nitriles, such as acetonitrile and benzonitrile; aromatic hydrocarbons, such as benzene and toluene; $C_6$–$C_{10}$ aliphatic and alicyclic hydrocarbons, such as n-hexane and cyclohexane; dimethylformamide; dimethyl sulfoxide; triethylamine; dimethoxyethane; dioxane; diglyme; and water.

When a cyclic aliphatic oxime is produced in the presence of a solvent, the concentration of the cyclic aliphatic amine as a reactant in the liquid phase is generally in the range of from 1 to 50% by weight, preferably from 3 to 30% by weight, based on the total weight of the solvent and the cyclic aliphatic amine. Depending on the type of amine used, too high a concentration of the amine may cause a disadvantage that the solid catalyst surface suffers marked discoloration (which is considered to be caused by the accumulation of the by-products on the catalyst surface), leading to a lowering of the catalyst activity. On the other hand, when the concentration of the amine is too low, the productivity of the cyclic aliphatic oxime per unit volume of a reactor used is decreased.

In the method of the present invention, the cyclic aliphatic primary amine is contacted with a solid catalyst in the liquid phase in the presence of a molecular oxygen-containing gas. The molecular oxygen-containing gas is either purified oxygen or a gaseous mixture of oxygen and an inert gas. Examples of inert gases include nitrogen, argon and helium. The "gaseous mixture" mentioned herein encompasses air. As the molecular oxygen-containing gas, it is preferred to use air or a gaseous mixture of oxygen and an inert gas. The molecular oxygen-containing gas may contain a small amount of moisture and/or $NH_3$.

When the gaseous mixture of oxygen and an inert gas is used as the molecular oxygen-containing gas, the molecular oxygen and the inert gas may be supplied to the reaction system in a desired ratio; however, it is preferred that the oxygen concentration is in a range such that the resultant gaseous phase does not have an explosive composition. The formation of the explosive composition can be avoided by strictly controlling the vapor pressures of the cyclic aliphatic amine and solvent and the like, and the concentrations of oxygen and the inert gas. Alternatively, irrespective of the concentration of flammable vapor in the gaseous phase, the formation of the explosive composition can be prevented by the use of a gaseous mixture of oxygen and an inert gas, wherein the concentration of oxygen is adjusted to be lower than the lower explosion limit.

The method of the present invention comprises subjecting a cyclic aliphatic primary amine to oxidation in the liquid phase. Therefore, it is required that the molecular oxygen (which has been introduced as a gas into the reaction system) be dissolved in a desired concentration in the liquid phase containing the catalyst, under the conditions for the oxidation. For this reason, for example, it is not preferred to employ a method in which an oxygen-containing gas is introduced into the reaction system under reduced pressure or atmospheric pressure and at a temperature wherein a liquid reaction mixture containing the reactant and the reaction product and/or the solvent is refluxed, because only a very small amount of oxygen can be dissolved in the liquid phase. The desired concentration of oxygen dissolved in the liquid phase can be achieved by contacting the oxygen-containing gas with the liquid phase under superatmospheric pressure.

With respect to the pressure of the reaction system, it is preferred that the total pressure (in terms of the absolute pressure) is in the range of from 500 to 15,000 kPa, more advantageously from 1,000 to 10,000 kPa, and that the partial pressure of oxygen is in the range of from 30 to 3,000 kPa, more advantageously from 60 to 2,000 kPa. When the oxidation is performed under low pressure conditions wherein the total pressure is lower than 500 kPa and the partial pressure of oxygen is lower than 30 kPa, the reaction rate tends to be lowered. On the other hand, when the oxidation is performed under high pressure conditions wherein the total pressure is higher than 15,000 kPa and the partial pressure of oxygen is higher than 3,000 kPa, the selectivity for a cyclic aliphatic oxime tends to be lowered. For example, when it is intended to perform the oxidation in a batchwise manner by using a gaseous mixture of oxygen and an inert gas, the oxidation may be performed by introducing a gaseous mixture having an appropriate oxygen concentration and an appropriate total pressure into the reaction system, wherein the oxygen concentration and the total pressure are determined, taking into consideration the amount of the cyclic aliphatic primary amine to be oxidized (or the amount of oxygen needed to oxidize the cyclic aliphatic primary amine) which varies depending on the type of catalyst and the reaction conditions.

In the method of the present invention, it is preferred that the reaction temperature is in the range of from 50 to 150° C., more advantageously from 60 to 145° C., most advantageously from 80 to 140° C. When the temperature exceeds 150° C., a gradual decomposition of the obtained oxime is promoted and a by-product having a high boiling point is formed in a higher ratio, thus lowering the selectivity for the desired oxime. On the other hand, when the temperature is lower than 50° C., the reaction rate tends to become low.

In the method of the present invention, as mentioned above, the cyclic aliphatic oxime is produced by subjecting a cyclic aliphatic primary amine to oxidation in the liquid phase under superatmospheric pressure in the presence of molecular oxygen and a solid catalyst. In the reaction system of the oxidation, the catalyst is heterogeneous, and the oxidation reaction site is present in the liquid phase; however, it is necessary to introduce oxygen into the reaction system by using a molecular oxygen-containing gas. Therefore, it is preferred that the liquid phase and the oxygen-containing gas satisfactorily contact with each other in the reaction system under pressure.

With respect to the manner of reaction, there is no particular limitation, and the oxidation reaction may be performed in any manner, such as a batchwise manner, a semi-batchwise manner and a continuous manner.

With respect to the method for introducing the molecular oxygen-containing gas into the reaction system, there is no particular limitation. For example, when the oxidation reaction is performed in a batchwise manner using a mixing-agitation type reaction vessel designed for use in a batchwise operation, the molecular oxygen-containing gas may be introduced either directly into the liquid phase which is formed in the reaction vessel, or into the gaseous phase (which is in contact with the liquid phase) in the reaction vessel. The molecular oxygen consumed in the reaction can be compensated by introducing purified oxygen, air or diluted oxygen gas into the reaction system either continuously or intermittently, so as to maintain a desired partial pressure of oxygen in the gaseous phase. Alternatively, when the oxidation is performed in a batchwise manner, by introducing an oxygen-containing gas into the reaction system, which gas contains oxygen in an amount sufficient for oxidizing a desired amount of the amine as the reactant, it becomes possible to continue the reaction without compensating for the consumed molecular oxygen until a desired conversion is achieved.

With respect to the shape of the solid catalyst used in the method of the present invention, there is no particular limitation; and the solid catalyst may have any of various shapes, such as a powder, a pulverized product, a particle and a cylinder, and an appropriate shape can be selected depending on the reaction process (a fixed-bed process, a fluidized-bed process, a catalyst suspension process or the like). With respect to the amount of the solid catalyst, there is no particular limitation, and the amount can be appropriately selected depending on the reaction manner (a batchwise manner, a semi-batchwise manner, a continuous manner or the like), the reaction process (a fixed-bed process, a fluidized-bed process, a catalyst suspension process or the like), the reaction temperature, the type of solvent and the type of solid catalyst.

For example, in the present invention, when the above-mentioned solid catalyst ($\alpha$) (comprising an oxide of at least one metal (a) and an oxide of at least one metal (b)) is used, and the oxidation is performed using a batchwise operation-type reactor in the liquid phase having the solid catalyst ($\alpha$) (in a powder form) suspended therein, it is preferred that the solid catalyst ($\alpha$) is used in an amount of from 0.05 to 50, in terms of a weight ratio of the solid catalyst ($\alpha$) to the cyclic aliphatic primary amine. Also in the case of the above-mentioned solid catalyst ($\beta$) (comprising an oxide of at least one metal (a) and an oxide of at least one metal (c)), it is preferred that the solid catalyst ($\beta$) is used in an amount of from 0.05 to 50, in terms of the weight ratio of solid catalyst ($\beta$) to the cyclic aliphatic primary amine.

With respect to the reaction time, it can be appropriately selected in accordance with the operation conditions, such as the reaction process, the reaction temperature and the amount of catalyst. Further, an appropriate reaction time can be also selected, based on a predetermined target yield of the cyclic aliphatic oxime. For example, when the oxidation is performed using a batchwise operation-type reactor in the liquid phase having powdery solid catalyst suspended therein, the reaction time is generally in the range of from about 0.5 to 10 hours.

In the method of the present invention, by employing oxidation conditions under which the conversion of a cyclic aliphatic amine is generally in the range of from 4 to 50%, preferably from 4 to 40%, more preferably from 4 to 30%, it becomes possible to produce a cyclic aliphatic oxime with advantageously high selectivity. The obtained cyclic aliphatic oxime can be recovered from the oxidation reaction mixture in the reaction vessel by a conventional method, for example, a distillation or a filtration. Generally, it is preferred that the unreacted cyclic aliphatic primary amine is recycled to the reaction vessel. When the method of the present invention is practiced on a commercial scale, in which the recycling of unreacted cyclic aliphatic primary amine is conducted, an improvement of the selectivity for a cyclic aliphatic oxime (i.e., the desired product) is by far more important and effective for improving the productivity of the cyclic aliphatic amine, as compared to an improvement of the conversion of the amine. (Even if the conversion is low, the yield of the desired product can be easily increased by recycling of the unreacted raw material so long as the selectivity for the desired product is high.)

By the method of the present invention, a cyclic aliphatic oxime can be generally produced with a selectivity as high as 50% or higher, preferably 70% or higher. In the present invention, after the oxidation, the solid catalyst can be easily separated from the resultant reaction mixture by filtration or the like. Thus, the method of the present invention requires no cumbersome operation for separation of the catalyst component from the reaction mixture, which operation is necessary in a method using a homogeneous catalyst.

Best Mode for Carrying Out the Invention

Hereinbelow, the present invention will be described in more detail with reference to the following Examples and Comparative Examples, which should not be construed as limiting the scope of the present invention.

In the Examples and Comparative Examples, various properties were measured and evaluated as follows.

(1) Determination of the amounts of metals contained in the solid catalyst

The amounts of metals contained in the solid catalyst were determined by means of a X-ray fluorescence analyzer (RIX-3000, manufactured and sold by Rigaku Corporation, Japan) under the following conditions.

X-Ray Excitation Conditions

Target element: Rh

Tube voltage: 50 kV

Tube current: 50 mA

Single crystal used for a monochromator:
polyethylene terephthalate for the determination of Al and Si, and
lithium fluoride for the determination of other metals Detector: scintillation counter Preparation of Samples A predetermined amount of the solid catalyst was mixed and diluted with a crystalline cellulose to obtain a powder mixture, and the obtained powder mixture was formed into tablets under a pressure of 20 tons by using a tableting machine in which the powder mixture was held by an aluminum ring.

Preparation of the Calibration Curve

With respect to each of the metal oxides used in the solid catalyst, tablets containing the metal oxide were produced in substantially the same manner as mentioned above, except that, instead of the solid catalyst, different amounts of the metal oxide were, respectively, used for producing the tablets. The obtained tablets were analyzed by X-ray fluorescence spectrometry to measure the intensities of the peaks ascribed to the metals, thereby obtaining a calibration curve for determination of the metal contents of the solid catalyst.

(2) Conversion of cyclohexylamine and selectivity for cyclohexanone oxime

The conversion of cyclohexylamine and the selectivity for cyclohexanone oxime, which were used for evaluating the results of the oxidation reaction of cyclohexylamine in the Examples and Comparative Examples, are defined by the following formulae, respectively.

$$\text{Conversion of cyclohexylamine}(\%) = \frac{\text{molar amount of reacted cyclohexylamine}}{\text{molar amount of fed cyclohexylamine}} \times 100$$

$$\text{Selectivity for cyclohexanone oxime }(\%) = \frac{\text{molar amount of produced cyclohexanone oxime}}{\text{molar amount of reacted cyclohexylamine}} \times 100$$

The reaction product was analyzed by gas chromatography. The gas chromatography was conducted using a gas chromatograph provided with capillary column (trade name: DB-1701, manufactured and sold by J&W Scientific, U.S.A.; length: 30 m) and a flame ionization detector (FID).

(3) Determination of concentrations of leached metals

The concentrations of metals leached from a solid catalyst into a liquid reaction mixture were determined by ICP emission spectrometry. As an ICP emission spectrometer, a spectrometer (JY 138, manufactured and sold by Rigaku Corporation, Japan) was used and the determination was conducted by operating a torch for an organic solvent at a high-frequency output of 1.4 kW.

EXAMPLE 1

<Preparation of a Solid Catalyst Comprised of Tungsten Oxide and Alumina>

10 g of a commercially available aluminum butoxide was placed in a glass beaker. Then, into the beaker was dropwise charged an aqueous solution of ammonium metatungstate (which had been prepared by dissolving 0.31 g of commercially available ammonium metatungstate in 5 g of water), while stirring by means of a glass rod. The resultant gel-like product was air-dried at room temperature for 1 hour, followed by vacuum-drying at 120° C. overnight. The resultant dried product was charged into a glass tubular furnace and calcined at 400° C. for 4 hours under atmospheric pressure, while feeding air into the furnace, thereby obtaining a catalyst comprised of tungsten oxide and alumina. The obtained catalyst was examined by the above-mentioned X-ray fluorescence spectrometry. As a result, it was found that the catalyst had a tungsten content of about 9% by weight.

<Oxidation Reaction of Cyclohexylamine>

1.4 g of cyclohexylamine and 14 g of t-butyl alcohol were charged into a high pressure autoclave having an internal volume of 100 ml, which was made of stainless steel SUS 316 and was equipped with a stirrer capable of introducing a gas into the autoclave, to thereby obtain a mixture. To the obtained mixture was added 0.14 g of the above-prepared tungsten oxide/alumina solid catalyst, to thereby obtain a suspension of the catalyst in the above-mentioned mixture. The inside of the autoclave was purged with nitrogen gas, and a gaseous mixture of nitrogen and oxygen (oxygen content=7% by volume) was introduced into the gaseous phase in the autoclave, so as to elevate the pressure in the autoclave to 6,000 kPa. At that time, the partial pressure of oxygen was 420 kPa. Then, the mixture in the autoclave was heated to 120° C., while stirring, to thereby perform an oxidation reaction for 4 hours to produce cyclohexanone oxime.

Further, the same procedure as mentioned above was repeated twice, except that the oxidation reaction time was changed to 6 hours and 8 hours. Thus, three runs of the production of cyclohexanone oxime were conducted, in which the reaction times in the three runs were 4 hours, 6 hours and 8 hours.

After completion of the reaction in each run, the resultant reaction mixture (slurry) having dispersed therein the catalyst was recovered from the autoclave, and subjected to a filtration using a suction filteration apparatus connected to an aspirator, to thereby separate the catalyst. Specifically, the reaction mixture (slurry) was dropwise added to a funnel on which a quantitative filter paper (No. 5C, manufactured and sold by Advantech Toyo Kaisha, Ltd., Japan) was placed, thereby collecting the solid catalyst on the filter paper and obtaining a liquid reaction mixture as a filtrate.

The obtained liquid reaction mixture was analyzed by gas chromatography. As a result, it was found that the cyclohexylamine conversions in the reactions conducted for 4 hours, 6 hours and 8 hours were 8.6%, 23.4% and 39.5%, respectively, and the selectivities for cyclohexanone oxime in the reactions conducted for 4 hours, 6 hours and 8 hours were 74.5%, 68.3% and 65.2%, respectively.

Further, the liquid reaction mixture was analyzed by ICP emission spectrometry. As a result, it was found that the concentration of tungsten which was dissolved from the solid catalyst into the reaction mixture was not more than 0.1 ppm.

As is apparent from the above results, by using the method of the present invention, cyclohexanone oxime could be produced with a selectivity as high as 60% or more. Further, by using a simple filtration method, the solid catalyst could be separated from the reaction mixture.

EXAMPLE 2

An oxidation reaction of cyclohexylamine was performed for 4 hours to produce cyclohexanone oxime in substantially the same manner as in Example 1, except that 14 g of n-butyl alcohol was used as a reaction solvent instead of t-butyl alcohol. As a result, it was found that the conversion of cyclohexylamine was 5.5% and the selectivity for cyclohexanone oxime was 50.2%.

EXAMPLE 3

An oxidation reaction of cyclohexylamine was performed for 4 hours to produce cyclohexanone oxime in substantially the same manner as in Example 1, except that 14 g of acetonitrile was used as a reaction solvent instead of t-butyl alcohol. As a result, it was found that the conversion of cyclohexylamine was 14.8% and the selectivity for cyclohexanone oxime was 74.0%.

EXAMPLE 4

An oxidation reaction of cyclohexylamine was performed for 4 hours in substantially the same manner as in Example 1, except that 14 g of benzonitrile was used as a reaction solvent instead of t-butyl alcohol, to thereby produce cyclohexanone oxime. As a result, it was found that the conversion of cyclohexylamine was 10.3% and the selectivity for cyclohexanone oxime was 67.7%.

EXAMPLE 5

An oxidation reaction of cyclohexylamine was performed for 4 hours in substantially the same manner as in Example 1, except that 14 g of cyclohexane was used as a reaction solvent instead of t-butyl alcohol, to thereby produce cyclohexanone oxime. As a result, it was found that the conversion of cyclohexylamine was 4.4% and the selectivity for cyclohexanone oxime was 63.3%.

EXAMPLE 6

An oxidation reaction of cyclohexylamine was performed for 4 hours in substantially the same manner as in Example 1, except that 14 g of water was used as a reaction solvent instead of t-butyl alcohol, to thereby produce cyclohexanone oxime. As a result, it was found that the conversion of cyclohexylamine was 5.8% and the selectivity for cyclohexanone oxime was 62.5%.

EXAMPLE 7

<Preparation of a Solid Catalyst Comprised of Alumina Having Supported thereon Tungsten Oxide>

A commercially available γ-alumina (manufactured and sold by Nishio Industry Co., Ltd., Japan; specific surface area: 282 m²/g) was vacuum-dried at 120° C. overnight, and the dried γ-alumina was used as a carrier for a solid catalyst. 1.42 g of ammonium paratungstate pentahydrate was dissolved into 60 g of water, followed by addition of 10 g of the dried γ-alumina, to thereby obtain a suspension.

The obtained suspension was charged into a glass-flask, and the flask was set in a rotary evaporator having an oil bath. In the rotary evaporator, the flask was immersed in the oil bath having a temperature of 90° C., and the content of the flask was slowly stirred under atmospheric pressure for 1.5 hours, to thereby obtain a slurry.

The obtained slurry was subjected to the following condensation-drying treatment. The temperature of the oil bath was elevated from 90° C. to 120° C. and the pressure in the flask was lowered slowly from atmospheric pressure to 20 kPa over about 2 hours, thereby evaporating water from the slurry in the flask. In accordance with the evaporation of water, the slurry became a cake-like product. Finally, the cake-like product was dried to form an agglomerated dry powder, which was composed of particles having different sizes as in the case of crushed particles.

The obtained agglomerated dry powder was vacuum-dried at 120° C. overnight and subjected to the following pulverization. The agglomerated dry powder was placed in a stainless steel mortar and ground by using a pestle. The resultant powder composed mainly of fine particles was transferred to an agate mortar and subjected to pulverization to further reduce the size of the particles. The resultant particles were passed through a sieve (mesh size: 75 μm) to collect particles having a diameter of 75 μm or less.

Then, the obtained particles were charged into a glass tubular furnace and calcined at 500° C. for 4 hours under atmospheric pressure, while feeding air into the furnace, thereby obtaining a solid catalyst comprised of alumina having supported thereon tungsten oxide. The tungsten content of the solid catalyst was about 9% by weight.

<Oxidation Reaction of Cyclohexylamine>

1.4 g of cyclohexylamine and 14 g of t-butyl alcohol were charged into the same high pressure autoclave as used in Example 1to obtain a mixture. To the obtained mixture was added 0.3 g of the above-prepared solid catalyst, to thereby obtain a suspension of the catalyst in the above-mentioned mixture. The inside of the autoclave was purged with nitrogen gas, and a gaseous mixture of nitrogen and oxygen (oxygen content=7% by volume) was introduced into the gaseous phase in the autoclave, so as to elevate the pressure in the autoclave to 7,000 kPa. At that time, the partial pressure of oxygen was 490 kPa. Then, the mixture in the autoclave was heated to 120° C., while stirring, to thereby perform an oxidation reaction for 4 hours to produce cyclohexanone oxime.

From the resultant reaction mixture, the solid catalyst was separated by filtration in the same manner as in Example 1, to obtain a liquid reaction mixture as a filtrate. The obtained liquid reaction mixture was analyzed by gas chromatography. As a result, it was found that the conversion of cyclohexylamine was 7.4% and the selectivity for cyclohexanone oxime was 65.0%.

Further, the liquid reaction mixture was analyzed by ICP emission spectrometry. As a result, it was found that the concentration of tungsten which was dissolved from the solid catalyst into the liquid reaction mixture was not more than 0.1 ppm.

As is apparent from the above results, also by the use of the solid catalyst comprised of alumina having supported thereon tungsten oxide, cyclohexanone oxime could be produced with a selectivity as high as 60% or more as in Example 1. Further, by using a simple filtration method, the solid catalyst could be separated from the reaction mixture.

EXAMPLE 8

<Preparation of the Solid Catalyst Comprised of Silica Having Supported thereon Tungsten Oxide>

A commercially available silica (AEROSIL-300, manufactured and sold by Nippon Aerosil Co., Ltd., Japan; specific surface area: 300 m$^2$/g) was vacuum-dried at 120° C. overnight, and the resultant dried silica was used as a carrier for a solid catalyst. 1.34 g of ammonium metatungstate was dissolved into 50 g of water, followed by addition of 10 g of the dried silica, to thereby obtain a suspension. By using the obtained suspension, a solid catalyst comprised of silica having supported thereon tungsten oxide was prepared in the same manner as in Example 7. The tungsten content of the obtained solid catalyst was about 9% by weight.

<Oxidation Reaction of Cyclohexylamine>

1.4 g of cyclohexylamine and 14 g of t-butyl alcohol were charged into the same high pressure autoclave as used in Example 1, to thereby obtain a mixture. To the obtained mixture was added 0.3 g of the above-prepared solid catalyst, to thereby obtain a suspension of the catalyst in the above-mentioned mixture. The inside of the autoclave was purged with nitrogen gas, and a gaseous mixture of nitrogen and oxygen (oxygen content=7% by volume) was introduced into the gaseous phase in the autoclave, so as to elevate the pressure in the autoclave to 7,000 kPa. At that time, the partial pressure of oxygen was 490 kPa. Then, the mixture in the autoclave was heated to 120° C., while stirring, to thereby perform an oxidation reaction for 4 hours to produce cyclohexanone oxime.

From the resultant reaction mixture, the solid catalyst was separated by filtration in the same manner as in Example 1 to obtain a liquid reaction mixture as a filtrate. The obtained liquid reaction mixture was analyzed by gas chromatography. As a result, it was found that the conversion of cyclohexylamine was 6.5% and the selectivity for cyclohexanone oxime was 51.7%.

EXAMPLE 9

<Preparation of the Solid Catalyst Comprised of a Silica-Alumina Carrier Having Supported thereon Tungsten Oxide>

A commercially available, shaped silica-alumina (N631HN, manufactured and sold by Nikki Chemical Co., Ltd., Japan; specific surface area: 400 m$^2$/g) was pulverized in the same manner as in Example 7 to obtain a silica-alumina powder. The obtained powder was vacuum-dried at 120° C. overnight to obtain a dried silica-alumina powder. 1.34 g of ammonium metatungstate was dissolved into 50 g of water, followed by addition of 10 g of the above-mentioned dried silica-alumina powder, to thereby obtain a suspension. By using the obtained suspension, a solid catalyst comprised of a silica-alumina carrier having supported thereon tungsten oxide was prepared in the same manner as in Example 7. The tungsten content of the obtained solid catalyst was about 9% by weight.

<Oxidation Reaction of Cyclohexylamine>

1.4 g of cyclohexylamine and 14 g of t-butyl alcohol were charged into the same high pressure autoclave as used in Example 1to thereby obtain a mixture. To the obtained mixture was added 0.3 g of the above-prepared solid catalyst, to thereby obtain a suspension of the catalyst in the above-mentioned mixture. The inside of the autoclave was purged with nitrogen gas, and a gaseous mixture of nitrogen and oxygen (oxygen content=7% by volume) was introduced into the gaseous phase in the autoclave, so as to elevate the pressure in the autoclave to 7,000 kPa. At that time, the partial pressure of oxygen was 490 kPa. Then, the mixture in the autoclave was heated to 120° C., while stirring, to thereby perform an oxidation reaction for 4 hours to produce cyclohexanone oxime.

From the resultant reaction mixture, the solid catalyst was separated by filtration in the same manner as in Example 1, to obtain a liquid reaction mixture as a filtrate. The obtained liquid reaction mixture was analyzed by gas chromatography. As a result, it was found that the conversion of cyclohexylamine was 6.0% and the selectivity for cyclohexanone oxime was 57.4%.

EXAMPLE 10

<Preparation of a Solid Catalyst Comprised of Alumina Having Supported thereon Niobium Oxide>

A commercially available γ-alumina (manufactured and sold by Nishio Industry Co., Ltd., Japan; specific surface area: 282 m$^2$/g) was vacuum-dried at 120° C. overnight, and the resultant dried γ-alumina was used as a carrier for a solid catalyst. 10.68 g of niobium hydrogenoxalate was dissolved into 45 g of an aqueous solution of oxalic acid, followed by addition of 10 g of the dried γ-alumina, to thereby obtain a suspension.

The obtained suspension was charged into a glass-flask and the flask was set in a rotary evaporator having an oil bath. In the rotary evaporator, the flask was immersed in the oil bath having a temperature of 90° C., and the content of the flask was slowly stirred under atmospheric pressure for 1.5 hours, to thereby obtain a slurry.

The obtained slurry was subjected to the following condensation-drying treatment. The temperature of the oil bath was elevated from 90° C. to 120° C. and the pressure in the flask was lowered slowly from atmospheric pressure to 20 kPa over about 2 hours, thereby evaporating water from the slurry in the flask. In accordance with the evaporation of water, the slurry became a cake-like product. Finally, the cake-like product was dried to form an agglomerated dry powder, which was composed of particles having different sizes as in the case of crushed particles.

The obtained agglomerated dry powder was vacuum-dried at 120° C. overnight and subjected to the following pulverization. The agglomerated dry powder was placed in a stainless steel mortar and ground by using a pestle. The resultant powder composed mainly of fine particles was transferred to an agate mortar and subjected to pulverization to further reduce the size of the particles. The resultant particles were passed through a sieve (mesh size: 75 μm) to collect particles having a diameter of 75 μm or less.

Then, the obtained particles were charged into a glass tubular furnace and calcined at 500° C. for 4 hours under atmospheric pressure, while feeding air into the furnace, thereby obtaining a solid catalyst comprised of alumina having supported thereon niobium oxide. The niobium content of the solid catalyst was about 9% by weight.

<Oxidation reaction of cyclohexylamine>

1.4 g of cyclohexylamine and 14 g of t-butyl alcohol were charged into the same high pressure autoclave as used in Example 1, to thereby obtain a mixture. To the obtained mixture was added 0.14 g of the above-prepared solid catalyst, to thereby obtain a suspension of the catalyst in the above-mentioned mixture. The inside of the autoclave was purged with nitrogen gas, and a gaseous mixture of nitrogen and oxygen (oxygen content=7% by volume) was introduced into the gaseous phase in the autoclave, so as to elevate the pressure in the autoclave to 6,000 kPa. At that time, the partial pressure of oxygen was 420 kPa. Then, the mixture in the autoclave was heated to 120° C., while stirring, to thereby perform an oxidation reaction for 4 hours to produce cyclohexanone oxime.

From the resultant reaction mixture, the solid catalyst was separated by filtration in the same manner as in Example 1, to obtain a liquid reaction mixture as a filtrate. The obtained liquid reaction mixture was analyzed by gas chromatography. As a result, it was found that the conversion of cyclohexylamine was 8.2% and the selectivity for cyclohexanone oxime was 64.4%.

Further, the liquid reaction mixture was analyzed by ICP emission spectrometry. As a result, it was found that the concentration of niobium which was dissolved solved from the solid catalyst into the liquid reaction mixture was not more than 0.1 ppm.

As is apparent from the above results, also by the use of the solid catalyst comprised of alumina having supported thereon niobium oxide, cyclohexanone oxime could be produced with a selectivity as high as 60% or more as same as in Examples 1 and 7. Further, by using a simple filtration method, the solid catalyst could be separated from the reaction mixture.

EXAMPLE 11
Preparation of the Solid Catalyst Comprised of Alumina Having Supported thereon Tungsten Oxide and Molybdenum Oxide A commercially available γ-alumina (manufactured and sold by Nishio Industry Co., Ltd., Japan; specific surface area 282 m$^2$/g) was vacuum-dried at 120° C. overnight, and the resultant dried γ-alumina was used as a carrier for a solid catalyst. 1.37 g of ammonium metatungstate and 0.185 g of ammonium paramolybdate were dissolved into 60 g of water, followed by addition of 10 g of the dried γ-alumina, to thereby obtain a suspension.

The obtained suspension was charged into a glass-flask and the flask was set in a rotary evaporator having an oil bath. In the rotary evaporator, the flask was immersed in the oil bath having a temperature of 90° C., and the content of the flask was slowly stirred under atmospheric pressure for 2 hours to obtain a slurry.

The obtained slurry was subjected to the following condensation-drying treatment. The temperature of the oil bath was elevated from 90° C. to 120° C. and the pressure in the flask was lowered slowly from atmospheric pressure to 20 kPa over about 2 hours to evaporate water from the slurry in the flask. In accordance with the evaporation of water, the slurry became a cake-like product. Finally, the cake-like product was dried to form an agglomerated dry powder, which was composed of particles having different sizes as in the case of crushed particles).

The obtained agglomerated dry powder was charged into a glass tubular furnace and dried at 120° C. for 5 hours under atmospheric pressure and under a flow of nitrogen gas. The dried powder was subjected to pulverization in the same manner as in Example 7 to obtain particles having diameters of 75 μm or less. The obtained particles were charged into a glass tubular furnace again and calcined at 500° C. for 4 hours under atmospheric pressure, while feeding air into the furnace, thereby obtaining a solid catalyst comprised of alumina having supported thereon tungsten oxide and molybdenum oxide. The tungsten content and molybdenum content of the solid catalyst were about 9% and about 1% by weight, respectively.

<Oxidation Reaction of Cyclohexylamine>

1.4 g of cyclohexylamine and 14 g of t-butyl alcohol were charged into the same high pressure autoclave as used in Example 1 to thereby obtain a mixture. To the obtained mixture was added 0.3 g of the above-prepared solid catalyst, to thereby obtain a suspension of the catalyst in the above-mentioned mixture. The inside of the autoclave was purged with nitrogen gas, and a gaseous mixture of nitrogen and oxygen (oxygen content=7% by volume) was introduced into the gaseous phase in the autoclave, so as to elevate the pressure in the autoclave to 7,000 kPa. At that time, the partial pressure of oxygen was 490 kPa. Then, the mixture in the autoclave was heated to 120° C., while stirring, to thereby perform an oxidation reaction for 4 hours to produce cyclohexanone oxime.

From the resultant reaction mixture, the solid catalyst was separated by filtration in the same manner as in Example 1 to obtain a liquid reaction mixture as a filtrate. The obtained liquid reaction mixture was analyzed by gas chromatography. As a result, it was found that the conversion of cyclohexylamine was 9.5% and the selectivity for cyclohexanone oxime was 58.7%.

EXAMPLE 12
<Preparation of the Solid Catalyst Comprised of Tungsten Oxide and Titania>

Ammonium metatungstate hydrate was dissolved in 200 g of water, followed by addition of 40 g of a commercially available amorphous titania (manufactured and sold by Wako Pure Chemical Co., Ltd., Japan; purity (in terms of $TiO_2$) : 99.9%), to thereby obtain a suspension slurry. The obtained suspension slurry was charged into a glass-flask, and the flask was set in a rotary evaporator having an oil bath. In the rotary evaporator, the flask was immersed in the oil bath having a temperature of 90° C., and the content of the flask was slowly stirred under atmospheric pressure for 1.5 hours to obtain a slurry.

The obtained slurry was subjected to the following condensation-drying treatment. The temperature of the oil bath was elevated from 90° C. to 120° C. and the pressure in the flask was lowered slowly from atmospheric pressure to 20 kPa over about 2 hours to evaporate water from the slurry in the flask. In accordance with the evaporation of water, the slurry became a cake-like product. Finally, the cake-like product was dried to form an agglomerated dry powder, which was composed of particles having different sizes as in the case of crushed particles.

The obtained agglomerated dry powder was vacuum-dried at 120° C. overnight and subjected to the following pulverization. The agglomerated dry powder was placed in a stainless steel mortar and ground by using a pestle. The resultant powder composed mainly of fine particles was transferred to an agate mortar and subjected to pulverization to further reduce the size of the particles. The resultant particles were passed through a sieve (mesh size: 75 μm) to collect particles having diameters of 75 μm or less.

Then, the obtained particles were charged into a glass tubular furnace and calcined at 500° C. for 4 hours under atmospheric pressure, while feeding air into the furnace, thereby obtaining a solid catalyst comprised of tungsten oxide and titania. The tungsten(W)/titanium(Ti) atomic ratio of the obtained solid catalyst was about 0.06.

<Oxidation Reaction of Cyclohexylamine>

1.4 g of cyclohexylamine and 14 g of t-butyl alcohol were charged into the same high pressure autoclave as used in Example 1 to thereby obtain a mixture. To the obtained mixture was added 0.28 g of the above-prepared solid catalyst, to thereby obtain a suspension of the catalyst in the above-mentioned mixture. The inside of the autoclave was purged with nitrogen gas, and a gaseous mixture of nitrogen and oxygen (oxygen content=7% by volume) was introduced into the gaseous phase in the autoclave, so as to elevate the pressure in the autoclave to 6,000 kPa. At that time, the partial pressure of oxygen was 420 kPa. Then, the mixture in the autoclave was heated to 120° C., while stirring, to thereby perform an oxidation reaction for 4 hours to produce cyclohexanone oxime.

From the resultant reaction mixture, the solid catalyst was separated by filtration in the same manner as in Example 1, to thereby obtain a liquid reaction mixture as a filtrate. The obtained liquid reaction mixture was analyzed by gas chromatography. As a result, it was found that the conversion of cyclohexylamine was 11.5% and the selectivity for cyclohexanone oxime was 71.8%.

Further, the liquid reaction mixture was analyzed by ICP emission spectrometry. As a result, it was found that the concentrations of tungsten(W) and titanium(Ti) which were leached from the solid catalyst into the reaction mixture were, respectively, not more than 0.1 ppm.

As is apparent from the above results, also by the use of the solid catalyst comprised of tungsten oxide and titania, cyclohexanone oxime could be produced with a selectivity as high as 70% or more. Further, by using a simple filtration method, the solid catalyst could be separated from the reaction mixture.

COMPARATIVE EXAMPLE 1

The preparation of a catalyst was conducted in substantially the same manner as in Example 12, except that ammonium metatungstate hydrate was not used and only the suspension slurry of the commercially available amorphous titania was used, thereby obtaining a solid titania catalyst (containing no tungsten oxide).

An oxidation reaction of cyclohexylamine was performed for 4 hours in substantially the same manner as in Example 1, except that 0.28 g of the above-prepared solid titania catalyst was used as a catalyst, to thereby produce cyclohexanone oxime.

From the resultant reaction mixture, the solid catalyst was separated by filtration in the same manner as in Example 1, to thereby obtain a liquid reaction mixture as a filtrate. The obtained liquid reaction mixture was analyzed by gas chromatography. As a result, it was found that the conversion of cyclohexylamine was 3.6% and the selectivity for cyclohexanone oxime was 50.2%.

EXAMPLE 13

An oxidation reaction of cyclohexylamine was performed for 4 hours in substantially the same manner as in Example 12, except that 14 g of acetonitrile was used as a reaction solvent instead of t-butyl alcohol, to thereby produce cyclohexanone oxime. As a result, it was found that the conversion of cyclohexylamine was 22.0% and the selectivity for cyclohexanone oxime was 71.3%.

EXAMPLE 14

An oxidation reaction of cyclohexylamine was performed for 4 hours in substantially the same manner as in Example 12, except that 14 g of benzonitrile was used as a reaction solvent instead of t-butyl alcohol, to thereby produce cyclohexanone oxime. As a result, it was found that the conversion of cyclohexylamine was 13.8% and the selectivity for cyclohexanone oxime was 58.7%.

EXAMPLE 15

An oxidation reaction of cyclohexylamine was performed for 4 hours in substantially the same manner as in Example 12, except that 14 g of water was used as a reaction solvent instead of t-butyl alcohol, to thereby produce cyclohexanone oxime. As a result, it was found that the conversion of cyclohexylamine was 17.1% and the selectivity for cyclohexanone oxime was 70.5%.

EXAMPLE 16

<Preparation of the Solid Catalyst Comprised of Tungsten Oxide and Zirconia>

Ammonium metatungstate hydrate was dissolved in 200 g of water, followed by addition of 30 g of a commercially available zirconia (trade name : RC-100, manufactured and sold by Daiichi Kigenso Kagaku Kogyo, Japan), to thereby obtain a suspension slurry. By using the obtained suspension slurry, a solid catalyst comprised of tungsten oxide and zirconia was prepared in the same manner as in Example 12. The tungsten(W)/zirconium(Zr) atomic ratio of the obtained solid catalyst was about 0.09.

<Oxidation Reaction of Cyclohexylamine>

1.4 g of cyclohexylamine and 14 g of t-butyl alcohol were charged into the same high pressure autoclave as used in Example 1 to thereby obtain a mixture. To the obtained mixture was added 0.30 g of the above-prepared solid catalyst, to thereby obtain a suspension of the catalyst in the above-mentioned mixture. The inside of the autoclave was purged with nitrogen gas, and a gaseous mixture of nitrogen and oxygen (oxygen content=7% by volume) was introduced into the gaseous phase in the autoclave, so as to elevate the pressure in the autoclave to 7,000 kPa. At that time, the partial pressure of oxygen was 490 kPa. Then, the mixture in the autoclave was heated to 120° C., while stirring, to thereby perform an oxidation reaction for 4 hours to produce cyclohexanone oxime.

From the resultant reaction mixture, the solid catalyst was separated by filtration in the same manner as in Example 1, to thereby obtain a liquid reaction mixture as a filtrate. The obtained liquid reaction mixture was analyzed by gas chromatography. As a result, it was found that the conversion of cyclohexylamine was 8.8% and the selectivity for cyclohexanone oxime was 73.6%.

Further, the liquid reaction mixture was analyzed by ICP emission spectrometry. As a result, it was found that the concentrations of tungsten(W) and zirconium(Zr) which were leached from the solid catalyst into the liquid reaction mixture were, respectively, not more than 0.1 ppm.

As is apparent from the above results, also by the use of the solid catalyst comprised of tungsten oxide and zirconia, cyclohexanone oxime could be produced with a selectivity as high as 70% or more. Further, by using a simple filtration method, the solid catalyst could be separated from the reaction mixture.

COMPARATIVE EXAMPLE 2

The preparation of a catalyst was conducted in substantially the same manner as in Example 16, except that ammonium metatungstate hydrate was not used and only the suspension slurry of the commercially available zirconia was used, thereby obtaining a solid zirconia catalyst (containing no tungsten oxide).

An oxidation reaction of cyclohexylamine was performed for 4 hours in substantially the same manner as in Example 1, except that 0.30 g of the above-prepared solid zirconia catalyst was used as a catalyst, to thereby produce cyclohexanone oxime.

From the resultant reaction mixture, the solid catalyst was separated by filtration in the same manner as in Example 1, to obtain a liquid reaction mixture as a filtrate. The obtained liquid reaction mixture was analyzed by gas chromatography. As a result, it was found that the conversion of cyclohexylamine was 1.2% and the selectivity for cyclohexanone oxime was 29.4%.

EXAMPLE 17
<Preparation of a Zirconia-Titania Compound Oxide Carrier>

In a glass reactor, a commercially available zirconium tetra-n-propoxide and a commercially available titanium tetraisopropoxide were dissolved into hexylene glycol (used in a molar amount which is about 2.5 times the total molar amount of zirconium tetra-n-propoxide and titanium tetraisopropoxide), and the resultant solution in the glass reactor was heated in an oil bath having a temperature of 120° C. for 3 hours, while stirring. Then, the temperature of the oil bath was elevated to 90° C., and an aqueous solution of ethanol was dropwise added to the above solution (in which the aqueous solution of ethanol was used in an amount such that the molar amount of water added to the solution became about 4 times as the total molar amount of zirconium tetra-n-propoxide and titanium tetraisopropoxide), to thereby hydrolyze the metal alkoxides to obtain a gel-like product. The gel-like product was subjected to aging overnight, followed by vacuum-drying at 130° C. The resultant dried gel was placed in a glass tubular furnace and calcined at 550° C. for 5 hours under atmospheric pressure, while feeding air into the furnace, thereby obtaining a white zirconia-titania compound oxide. The zirconium(Zr)/titanium(Ti) atomic ratio of the obtained compound oxide was about 1.0.

<Preparation of a Solid Catalyst Comprised of Tungsten Oxide and the Zirconia-Titania Compound Oxide>

Ammonium metatungstate hydrate was dissolved in 200 g of water, followed by addition of 30 g of the above-prepared zirconia-titania compound oxide, to thereby obtain a suspension slurry. By using the obtained suspension slurry, a solid catalyst was prepared in the same manner as in Example 12, thereby obtaining a solid catalyst comprised of tungsten oxide and the zirconia-titania compound oxide. The tungsten(W)/(titanium(Ti)+zirconium(Zr)) atomic ratio of the obtained solid catalyst was about 0.08.

<Oxidation Reaction of Cyclohexylamine>

An oxidation reaction of cyclohexylamine was performed for 4 hours in substantially the same manner as in Example 1, except that 0.28 g of the above-prepared solid catalyst was used as a solid catalyst, to thereby produce cyclohexanone oxime.

From the resultant reaction mixture, the solid catalyst was separated by filtration in the same manner as in Example 1, to thereby obtain a liquid reaction mixture as a filtrate. The obtained liquid reaction mixture was analyzed by gas chromatography. As a result, it was found that the conversion of cyclohexylamine was 10.9% and the selectivity for cyclohexanone oxime was 72.2%.

As is apparent from the above results, also by the use of the solid catalyst comprised of tungsten oxide and a zirconia-titania compound oxide, cyclohexanone oxime could be produced with a selectivity as high as 70% or more as in Examples 12 and 16.

COMPARATIVE EXAMPLE 3

An oxidation reaction of cyclohexylamine was performed for 4 hours in substantially the same manner as in Example 1, except that 0.28 g of a zirconia-titania composite oxide (containing no tungsten oxide) prepared by the same method as in Example 17 was used as a solid catalyst.

From the resultant reaction mixture, the solid catalyst was separated by filtration in the same manner as in Example 1, to thereby obtain a liquid reaction mixture as a filtrate. The obtained liquid reaction mixture was analyzed by gas chromatography. As a result, it was found that the conversion of cyclohexylamine was 6.5% and the selectivity for cyclohexanone oxime was 48.0%.

EXAMPLE 18
<Preparation of a Solid Catalyst Comprised of Tungsten Oxide and Titania>

10.5 g of a commercially available titanium tetraisopropoxide was placed in a glass beaker. Then, into the beaker was dropwise charged an aqueous solution of ammonium metatungstate (which had been prepared by dissolving 0.93 g of ammonium metatungstate in 13.2 g of hot water), while stirring by means of a glass rod, thereby obtaining a gel-like product. The resultant gel-like product was air-dried at room temperature for about 4 hours, followed by vacuum-drying at 120° C. overnight. The resultant dried product was charged into a glass tubular furnace and calcined at 400° C. for 4 hours under atmospheric pressure, while feeding air into the furnace, thereby obtaining a solid catalyst comprised of tungsten oxide and titania. The tungsten(W)/titanium(Ti) atomic ratio of the obtained solid catalyst was about 0.10.

<Oxidation Reaction of Cyclohexylamine>

1.4 g of cyclohexylamine and 12 g of t-butyl alcohol were charged into the same high pressure autoclave as used in Example 1 to thereby obtain a mixture. To the obtained mixture was added 0.28 g of the above-prepared solid catalyst, to thereby obtain a suspension of the catalyst in the above-mentioned mixture. The inside of the autoclave was purged with nitrogen gas, and a gaseous mixture of nitrogen and oxygen (oxygen content=7% by volume) was introduced into the gaseous phase in the autoclave, so as to elevate the pressure in the autoclave to 6,000 kPa. At that time, the partial pressure of oxygen was 420 kPa. Then, the mixture in the autoclave was heated to 120° C., while stirring, to thereby perform an oxidation reaction for 4 hours to produce cyclohexanone oxime.

From the resultant reaction mixture, the solid catalyst was separated by filtration in the same manner as in Example 1, to thereby obtain a liquid reaction mixture as a filtrate. The obtained liquid reaction mixture was analyzed by gas chromatography. As a result, it was found that the conversion of cyclohexylamine was 18.1% and the selectivity for cyclohexanone oxime was 69.5%.

Further, the liquid reaction mixture was analyzed by ICP emission spectrometry. As a result, it was found that the concentrations of tungsten(W) and titanium(Ti) which were leached from the solid catalyst into the reaction mixture were, respectively, not more than 0.1 ppm.

As is apparent from the above results, also by the use of the solid catalyst comprised of tungsten oxide and titania, cyclohexanone oxime could be produced with a selectivity as high as 60% or more as in Examples 1, 7 and 10. Further, by using a simple filtration method, the solid catalyst could be separated from the reaction mixture.

EXAMPLE 19

<Preparation of a solid catalyst comprised of niobium oxide and titania>

10.5 g of a commercially available titanium tetraisopropoxide and 0.4 g of a commercially available niobium pentaethoxide were charged into a glass beaker and mixed together to prepare a uniform alkoxide mixture solution. To the solution was dropwise added 13.8 g of deionized water, while stirring by means of a glass rod, thereby obtaining a gel-like product. The obtained gel-like product was air-dried at room temperature for 4 hours, followed by vacuum-drying at 120° C. overnight. The resultant dried product was charged into a glass-made tubular furnace and calcined at 400° C. for 4 hours under atmospheric pressure, while feeding air into the furnace, thereby obtaining a solid catalyst comprised of niobium oxide and titania. The niobium(Nb)/titanium(Ti) atomic ratio of the obtained solid catalyst was about 0.035.

<Oxidation Reaction of Cyclohexylamine>

An oxidation reaction of cyclohexylamine was performed for 4 hours in substantially the same manner as in Example 1, except that 0.28 g of the above-prepared solid catalyst was used, to thereby produce cyclohexanone oxime.

From the resultant reaction mixture, the solid catalyst was separated by filtration in the same manner as in Example 1 to obtain a liquid reaction mixture as a filtrate. The obtained liquid reaction mixture was analyzed by gas chromatography. As a result, it was found that the conversion of cyclohexylamine was 7.8% and the selectivity for cyclohexanone oxime was 61.7%.

Further, the liquid reaction mixture was analyzed by ICP emission spectrometry. As a result, it was found that the concentrations of niobium(Nb) and titanium(Ti) which were leached from the solid catalyst into the reaction mixture were, respectively, not more than 0.1 ppm.

As is apparent from the above results, also by the use of the solid catalyst comprised of niobium oxide and titania, cyclohexanone oxime could be produced with a selectivity as high as 60% or more as in Examples 1, 7, 10 and 18. Further, by using a simple filtration method, the solid catalyst could be separated from the reaction mixture.

EXAMPLE 20

<Preparation of a Solid Catalyst Comprised of Tantalum Oxide and Titania>

The preparation of a solid catalyst was conducted in substantially the same manner as in Example 19, except that 0.52 g of tantalum pentaethoxide was used instead of niobium pentaethoxide, thereby obtaining a solid catalyst comprised of tantalum oxide and titania. The tantalum(Ta)/titanium(Ti) molar ratio of the obtained solid catalyst was about 0.035.

<Oxidation Reaction of Cyclohexylamine>

An oxidation reaction of cyclohexylamine was performed for 4 hours in substantially the same manner as in Example 18, except that 0.28 g of the above-prepared solid catalyst was used, to thereby produce cyclohexanone oxime.

From the resultant reaction mixture, the solid catalyst was separated by filtration in the same manner as in Example 1 to obtain a liquid reaction mixture as a filtrate. The obtained liquid reaction mixture was analyzed by gas chromatography. As a result, it was found that the conversion of cyclohexylamine was 7.6% and the selectivity for cyclohexanone oxime was 63.8%.

Further, the liquid reaction mixture was analyzed by ICP emission spectrometry. As a result, it was found that the concentrations of tantalum(Ta) and titanium(Ti) which were leached from the solid catalyst into the reaction mixture were, respectively, not more than 0.1 ppm.

As is apparent from the above results, also by the use of the solid catalyst comprised of tantalum oxide and titania, cyclohexanone oxime could be produced with a selectivity as high as 60% or more as same as in Example 1, 7, 10, 18 and 19. Further, by using a simple filtration method, the solid catalyst could be separated from the reaction mixture.

COMPARATIVE EXAMPLE 4

<Preparation of a Titania Solid Catalyst>

10.5 g of a commercially available titanium tetraisopropoxide was placed in a glass beaker. Then, into the beaker was dropwise charged 13.8 g of deionized water while stirring by means of a glass rod, thereby obtaining a gel-like product. By using the obtained gel-like product, a titania solid catalyst was prepared in substantially the same manner as in Example 18.

<Oxidation Reaction of Cyclohexylamine>

An oxidation reaction was performed for 4 hours in substantially the same manner as in Example 18, except that 0.28 g of the above-prepared solid catalyst was used, thereby obtaining cyclohexanone oxime.

From the resultant reaction mixture, the solid catalyst was separated by filtration in substantially the same manner as in Example 1 to obtain a liquid reaction mixture as a filtrate. The obtained liquid reaction mixture was analyzed by gas chromatography. As a result, it was found that the conversion of cyclohexylamine was 4.3%, and the selectivity for cyclohexanone oxime was 45.5%.

COMPARATIVE EXAMPLE 5

(The Method as Described in EP 395046)

<Preparation of a Titania Solid Catalyst>

10 g of a commercially available titanium tetraisopropoxide was placed in a glass beaker. Then, into the beaker was slowly dropwise charged 10 g of water while stirring by means of a glass rod, and the resultant mixture was continuously stirred at room temperature for about 4 hours, thereby obtaining a precipitate. The obtained precipitate was washed with water. Then, the washed precipitate was charged into a glass tubular furnace, and dried at 120° C. for 12 hours, and then at 200° C. for 2 hours, under atmospheric pressure under a flow of nitrogen gas, thereby obtaining a dried precipitate. The obtained dried precipitate was subjected to pulverization in substantially the same manner as in Example 7, thereby obtaining a powdery solid catalyst having a particle diameter of 75 μm or less.

<Oxidation Reaction of Cyclohexylamine>

2.97 g of cyclohexylamine and 7 ml of diglyme were charged into a high pressure autoclave (internal volume: 100 ml) which was made of SUS316 stainless steel and was equipped with a magnetic stirrer, to thereby obtain a mixture. Then, 0.4 g of the above-prepared solid catalyst was dispersed in the obtained mixture. The inside of the autoclave was purged with nitrogen gas, and purified oxygen was introduced into the gaseous phase in the autoclave, so as to elevate the total pressure in the autoclave to 3,140 kPa. Then, the mixture in the autoclave was heated to 120° C., while stirring, to thereby perform an oxidation reaction for 4 hours to produce cyclohexanone oxime.

From the resultant reaction mixture, the solid catalyst was separated by filtration in the same manner as in Example 1 to obtain a liquid reaction mixture as a filtrate. The obtained liquid reaction mixture was analyzed by gas chromatography. As a result, it was found that the conversion of cyclohexylamine was 31.2%, and the selectivity for cyclohexanone oxime was 22.5%.

By the method of this Comparative Example, the catalyst could be separated from the obtained liquid reaction mixture by using a simple filtration method; however, the selectivity for cyclohexanone oxime was as low as 22.5%.

INDUSTRIAL APPLICABILITY

The method of the present invention is advantageous not only in that the oxidizing agent employed is molecular oxygen which is much safer than other oxidizing agents (such as hydrogen peroxide and an organic hydroperoxide), but also in that it becomes possible to produce a cyclic aliphatic oxime in the liquid phase with high selectivity. Further, since a solid catalyst is used in the method of the present invention, the separation and recovery of the catalyst from the reaction mixture can be very easily performed after the reaction without any cumbersome operations. Therefore, the method of the present invention is commercially very advantageous.

What is claimed is:

1. A method for producing a cyclic aliphatic oxime, which comprises subjecting a cyclic aliphatic primary amine to oxidation in the liquid phase under superatmospheric pressure in the presence of molecular oxygen and a solid catalyst, wherein said solid catalyst comprises an oxide of at least one metal (a) selected from the group consisting of metals belonging to Groups 5 and 6 of the Periodic Table.

2. The method according to claim 1, wherein said cyclic aliphatic primary amine is cyclohexylamine.

3. The method according to claim 1 or 2, wherein said solid catalyst further comprises an oxide of at least one metal (b) selected from the group consisting of metals belonging to Groups 2, 13 and 14 of the Periodic Table.

4. The method according to claim 3, wherein said metal (a) is at least one metal selected from the group consisting of niobium and tungsten.

5. The method according to claim 3, wherein said metal (a) is tungsten.

6. The method according to claim 3, wherein said metal (b) is at least one metal selected from the group consisting of aluminum and silicon.

7. The method according to claim 1, wherein the content of said metal (a) in said solid catalyst is from 1 to 60% by weight.

8. The method according to claim 1 or 2, wherein said solid catalyst further comprises an oxide of at least one metal (c) selected from the group consisting of metals belonging to Group 4 of the Periodic Table.

9. The method according to claim 8, wherein said metal (a) is at least one metal selected from the group consisting of niobium, tantalum and tungsten.

10. The method according to claim 8, wherein said metal (a) is tungsten.

11. The method according to claim 8, wherein said metal (c) is at least one metal selected from the group consisting of titanium and zirconium.

12. The method according to claim 8, wherein the atomic ratio of said metal (a) to said metal (c) is in the range of from 0.01 to 1.0.

* * * * *